(12) United States Patent
Roth

(10) Patent No.: US 7,181,986 B2
(45) Date of Patent: Feb. 27, 2007

(54) QUALITY CONTROL METHODS FOR GAS DIFFUSION MEDIA

(75) Inventor: Joerg Roth, Trebur (DE)

(73) Assignee: General Motors Corporation, Detroit, MI (US)

(*) Notice: Subject to any disclaimer, the term of this patent is extended or adjusted under 35 U.S.C. 154(b) by 0 days.

(21) Appl. No.: 11/249,663

(22) Filed: Oct. 13, 2005

(65) Prior Publication Data

US 2006/0037416 A1 Feb. 23, 2006

Related U.S. Application Data

(62) Division of application No. 10/342,898, filed on Jan. 15, 2003, now Pat. No. 7,107,864.

(51) Int. Cl.
*G01N 11/00* (2006.01)

(52) U.S. Cl. .................................................... 73/866

(58) Field of Classification Search .............. 73/866, 73/38, 64.47
See application file for complete search history.

(56) References Cited

U.S. PATENT DOCUMENTS

| 5,346,780 A | 9/1994 | Suzuki |
| 5,763,113 A | 6/1998 | Meltser et al. |
| 6,103,077 A | 8/2000 | DeMarinis et al. |
| 6,329,094 B1 | 12/2001 | Yasuo et al. |
| 6,350,539 B1 | 2/2002 | Wood, III et al. |
| 6,406,807 B1 | 6/2002 | Nelson et al. |
| 6,444,602 B1 | 9/2002 | DeMarinis et al. |
| 6,928,893 B2 | 8/2005 | Roth .................. 73/866 |
| 2002/0134501 A1 | 9/2002 | Fan et al. |
| 2003/0104267 A1 | 6/2003 | Haridoss et al. |
| 2004/0187565 A1* | 9/2004 | Sutton .................. 73/104 |

FOREIGN PATENT DOCUMENTS

| EP | 0 731 520 | 11/1996 |
| WO | WO 97/50143 | 12/1997 |

* cited by examiner

*Primary Examiner*—Daniel S. Larkin
(74) *Attorney, Agent, or Firm*—Charles H. Ellerbrock

(57) ABSTRACT

The present invention discloses various methods in which a quality of a diffusion media for use in a fuel cell assembly can be qualitatively evaluated. The material constant, an internal contact angle, a ratio of high and low energy pores, and an external contact angle can be calculated for the diffusion media and compared to a predetermined standard to evaluate the quality of the diffusion media.

19 Claims, 5 Drawing Sheets

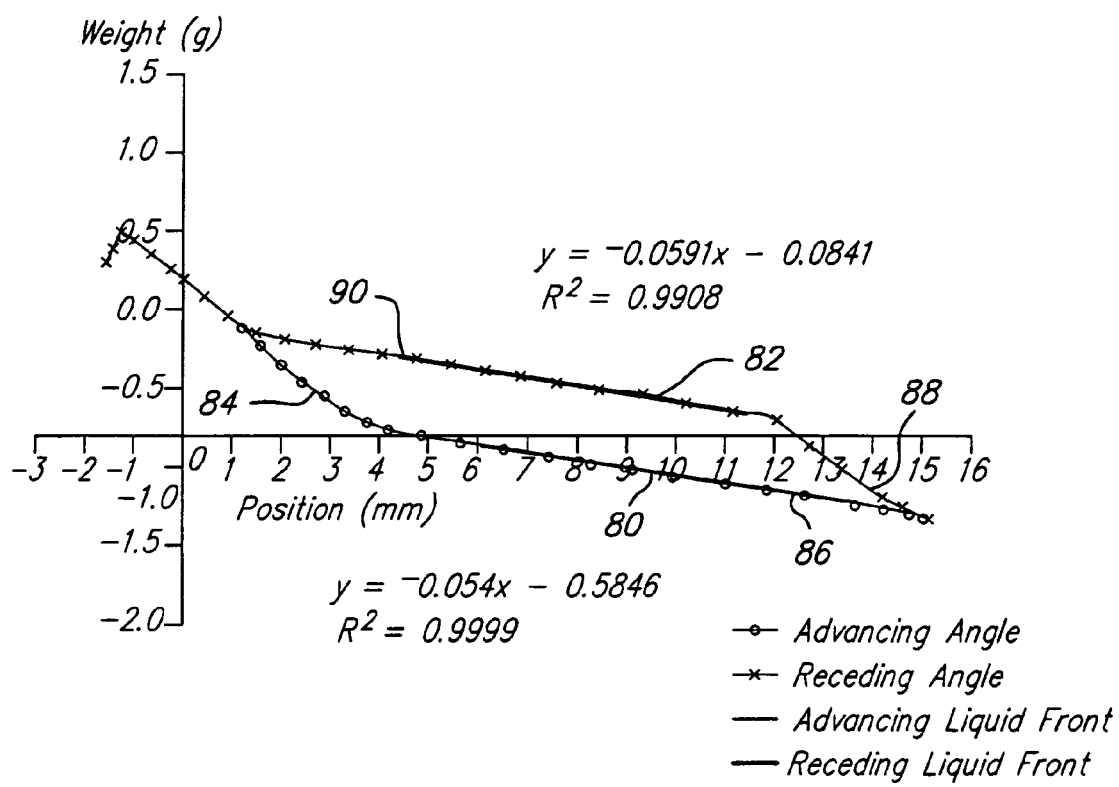
Wilhelmy Plot For Sample With Micro Porous Coating
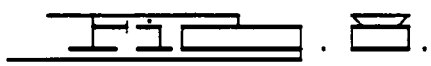

QUALITY CONTROL METHODS FOR GAS DIFFUSION MEDIA

CROSS-REFERENCE TO RELATED APPLICATIONS

This application is a divisional of U.S. patent application Ser. No. 10/342,898, filed on Jan. 15, 2003 now U.S. Pat. No. 7,107,864, the disclosure of which is incorporated herein by reference.

FIELD OF THE INVENTION

The present invention relates to fuel cells that use a gas diffusion media and, more particularly, to quality control methods for gas diffusion media.

BACKGROUND OF THE INVENTION

Fuel cells have been used as a power source in many applications and have been proposed for use in electrical vehicular power plants to replace internal combustion engines. In proton exchange membrane (PEM) type fuel cells, hydrogen is supplied to the anode of the fuel cell and oxygen is supplied as the oxidant to the cathode. PEM fuel cells include a membrane electrode assembly (MEA) comprising a thin, proton transmissive, non-electrically conductive solid polymer electrolyte membrane having the anode on one of its faces and the cathode on the opposite face. The MEA is sandwiched between a pair of electrically conductive elements which (1) serve as current collectors for the anode and cathode, and (2) contain appropriate channels and/or openings therein for distributing the fuel cell's gaseous reactants over the surfaces of the respective anode and cathode catalysts. A plurality of individual cells are commonly bundled together to form a PEM fuel cell stack. The term fuel cell is typically used to refer to either a single cell or a plurality of cells (stack) depending on the context. A group of cells within the stack is referred to as a cluster. Typical arrangements of multiple cells in a stack are described in U.S. Pat. No. 5,763,113, assigned to General Motors Corporation.

In PEM fuel cells hydrogen ($H_2$) is the anode reactant (i.e., fuel) and oxygen is the cathode reactant (i.e., oxidant). The oxygen can be either a pure form ($O_2$), or air (a mixture of $O_2$ and $N_2$). The solid polymer electrolytes are typically made from ion exchange resins such as perfluoronated sulfonic acid. The anode/cathode typically comprises finely divided catalytic particles, which are often supported on carbon particles, and admixed with a proton conductive resin. The catalytic particles are typically costly precious metal particles. These membrane electrode assemblies, which comprise the catalyzed electrodes, are relatively expensive to manufacture and require certain controlled conditions in order to prevent degradation thereof.

Efficient operation of a fuel cell depends on the ability to effectively disperse reactant gases at catalytic sites of the electrode where reaction occurs. In addition, effective removal of reaction products is required so as to not inhibit flow of fresh reactants to the catalytic sites. Therefore, it is desirable to improve the mobility of reactant and product species to and from the MEA where reaction occurs.

To improve the mobility of reactant and product species to and from the MEA where reactions occur, a diffusion structure which enhances mass transport to and from an electrode in a MEA of a fuel cell is used. The diffusion structure cooperates and interacts with an electrode at a major surface of the electrode opposite the membrane electrolyte of the cell, therefore, electrical and heat conductivity are required. The diffusion structure is typically a composite diffusion medium which facilitates the supply of reactant gas to the electrode. The diffusion structure also facilitates movement of water and the products of the reactions. The typical diffusion structure includes a characteristic bulk layer having two or more portions, such as a PTFE coating and/or a microporous layer, each with various properties, including hydrophobicity and surface energy. The bulk layer is also usable alone to function as a diffusion structure. However, it is preferably combined within an absorption layer and a desorption layer on respective sides of the bulk layer to form a preferred diffusion structure. The diffusion structure, either the bulk layer alone or combined with other layers, is hereinafter referred to as a diffusion media. See for example U.S. Pat. No. 6,350,539 issued to the assignee of the present application. The diffusion media is positioned between the MEA and the cathode or anode flow channels of an individual fuel cell.

The quality of a diffusion media is hard to control due to there only being a few tests indicating the performance of a diffusion media. During the manufacturing of a diffusion media, there can be several steps. A first step can include a hydrophobization step, such as teflonization of the bulk layer (applying PTFE to the bulk layer) or coating the bulk layer with other low surface energy substance(s) and a second step can include coating the hydrophobized bulk layer with a microporous substrate. To date, the PTFE content is routinely checked by weight and/or by fluorine mapping using a scanning electronic microscope (SEM). The coating can also be visually checked. The weight check is not very significant due to averaging the weight gain for the whole sheet (bulk layer). That is, the amount of PTFE at any given location is not known; rather, the total amount of PTFE on the bulk layer is determined and used to calculate an average PTFE content on a per unit basis. Thus, the weight check can not identify specific areas of the diffusion media that have an undesirable PTFE content nor provide a quantitative measure indicative of performance and surface energy. Fluorine mapping is not always desirable because it is expensive and time consuming. The visual test can identify contrasting dark and light spots in the diffusion media coating which are indicative of problems during fabrication. The visual test, however, is a qualitative check that is only useful in spotting large area defects. For controlling the microporous layer, the weight and the gas flow through the diffusion media can be checked for quality control. Additionally, the thickness of the microporous layer can be used for quality assurance purposes. These methods, however, do not appear to adequately relate to the properties effecting the performance of the diffusion media in a fuel cell. Thus, an improved method for quality control is needed.

SUMMARY OF THE INVENTION

The present invention discloses novel techniques to determine quality of a diffusion media. The quality determination is based on properties affecting performance of the diffusion media in a fuel cell. More particularly, quality is based upon the property of surface energy, also related to wettability and liquid handling. The novel techniques measure liquid handling properties of diffusion media directly and more preferably, quantitatively.

In one aspect of the present invention, a method of determining a quality of a diffusion media for use in a fuel cell is disclosed. The method includes the steps of: (1) determining a material constant for a diffusion media based on imbibing of a complete wetting liquid by said diffusion media; and (2) comparing the material constant to a predetermined standard.

In another aspect of the present invention a different method of determining a quality of a diffusion media for use in a fuel cell is disclosed. The method includes the steps of: (1) determining an internal contact angle of a diffusion media based on imbibing of a partial wetting liquid by said diffusion media; and (2) comparing the internal contact angle with a predetermined standard.

In a different aspect of the present invention, yet another method of determining a quality of a diffusion media for use in a fuel cell is disclosed. The method includes the steps of: (1) determining a ratio of a volume high energy pores in at least a portion of a diffusion media and a volume of low energy pores in the same portion of the diffusion media; and (2) comparing the ratio with a predetermined standard.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 8 is a graph of experimental data of a weight change of a PTFE coated diffusion media with a microporous layer as a function of position when dipped in a non-wetting liquid.

DETAILED DESCRIPTION OF THE PREFERRED EMBODIMENTS

The following description of the preferred embodiments is merely exemplary in nature and is in no way intended to limit the invention, its application, or uses.

Figure 1:
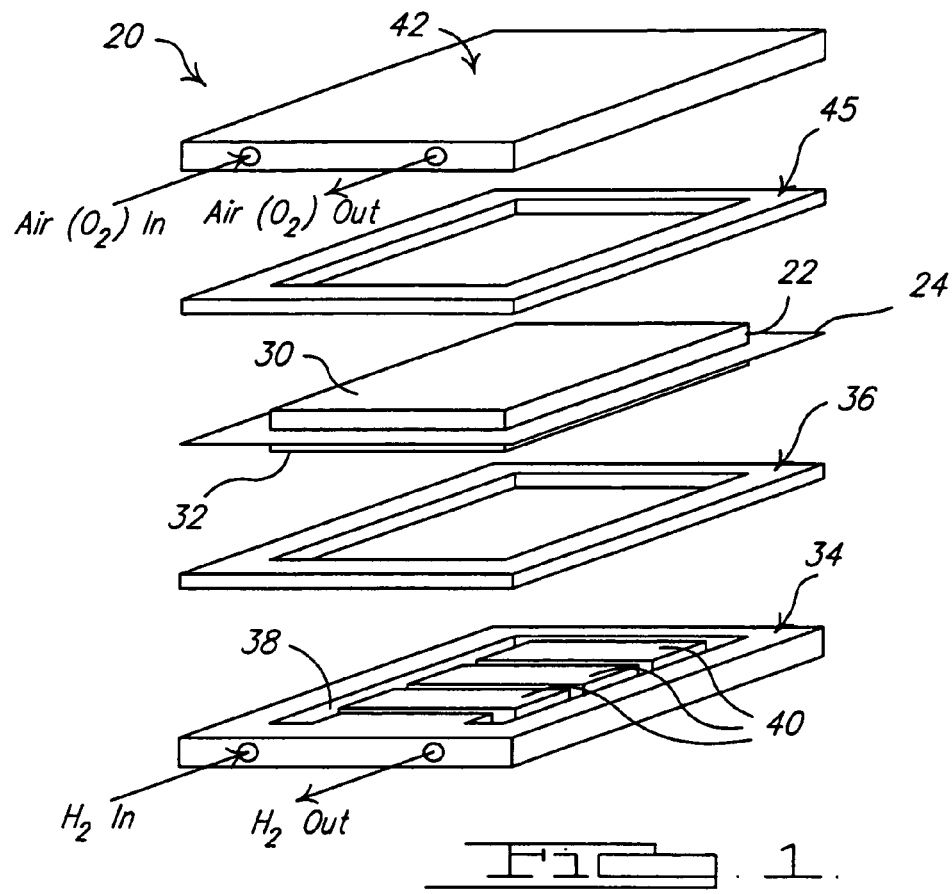
FIG. 1 is a schematic view of an unassembled fuel cell assembly which includes a membrane electrode assembly and diffusion media.
Figure 2:
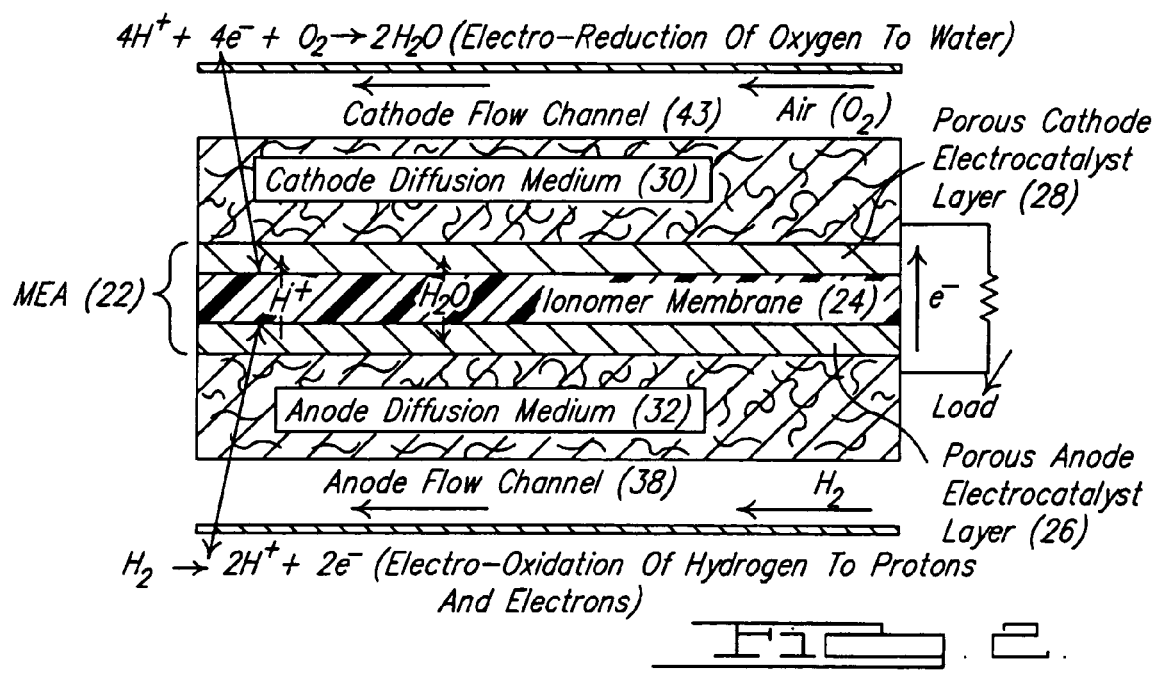
FIG. 2 is a pictorial illustration of a cross-section of a membrane electrode assembly.

The present invention provides a variety of methods for testing a quality of a diffusion media that can be used in a fuel cell assembly, such as the proton exchange membrane (PEM) fuel cell assembly 20 shown in FIG. 1. Referring to FIGS. 1 and 2, the fuel cell assembly 20 comprises a membrane electrode assembly 22 which comprises an ionomer membrane 24. An anode electrode 26 is on one side of the membrane 24, and a cathode electrode 28 is on the other side. A cathode diffusion media 30 is on the side of cathode electrode 28 facing away from membrane 24. An anode diffusion media 32 is on the side of the anode electrode 26 facing away from membrane 24. The anode side further includes a plate 34 which serves as a gas distributor and current collector. Plate 34 may be an end plate or a bipolar plate that serves to separate adjacent cells in a fuel cell stack. Optionally, a gasket 36 is included between membrane 24 and plate 34. Plate 34 has surface features in the form of recesses which provide a fuel gas flow channel 38 and un-recessed features referred to as lands 40. The cathode side is similarly configured with a plate 42 having surface features in the form of recesses which provide an oxidant gas flow channel 43 and un-recessed features referred to as lands 44, and is electrically conductive. Optionally, a gasket 45 is included between membrane 24 and plate 42.

Figure 3:
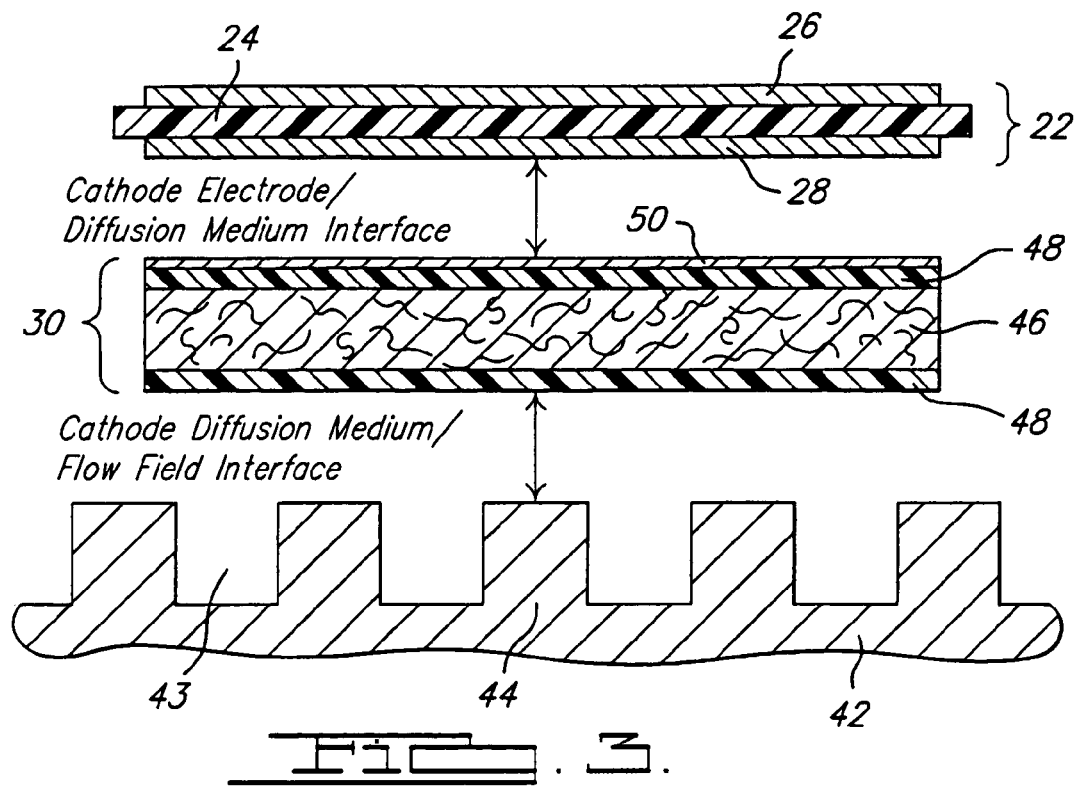
FIG. 3 is an exploded cross-sectional view of a multilayered cathode diffusion media.

Diffusion media 30 and 32 provide an important function in the operation of the fuel cell assembly 20. Diffusion media 30 and 32 cooperate with electrodes 26 and 28 and plates 34 and 42 which have flow field channels (grooves) 38 and 43 to promote the transport and removal of water and gases, as well as heat and electrons, to and from fuel cell assembly 20. Referring now to FIG. 3, it can be seen that diffusion media 30 and 32 can be comprised of multiple components or layers. While only the cathode diffusion media 30 is shown in FIG. 3, it should be understood that anode diffusion media 32 can be comprised of similar or different components and layers, as needed, to provide desired properties. Diffusion media 30 has a base material 46 on which additional layers or coatings can be applied to facilitate and enhance the functioning of diffusion media 30. For example, base material 46 can be provided with a polytetrafluoroethylene (PTFE) coating 48 to provide desired characteristics and properties for diffusion media 30. Additionally, a microporous layer 50 can also be applied to one or more of the surfaces of diffusion media 30 to again provide desired characteristics and properties for diffusion media 30. Specifics about desired properties of diffusion media and materials of construction can be found in U.S. Pat. No. 6,350,539 to Wood, III et al., entitled "Composite Gas Distribution Structure for Fuel Cell," which is incorporated herein by reference. Different ways of applying coatings and/or layers to a diffusion media are described in International Publication No. WO 97/50143, entitled "Gas Diffusion Electrode," and in European Patent Application EP 0731520, entitled "Materials for Use in Catalytic Electrode Manufacture" the disclosures of which are incorporated by reference herein.

By the present invention, it has been determined that the surface energy of the diffusion media is indicative of the performance of the diffusion media in facilitating the mobility of reactants to and from the MEA. Diffusion media, however, are sensitive to changes in the surface energy. The changes in the surface energy can be caused by a variety of things. For example, finger grease from handling the diffusion media or other contaminants can change the surface energy. Additionally, deviation in a process parameter (e.g., temperature, concentration, time, etc.) during manufacturing especially during coating operations can also change the surface energy of the diffusion media. When the surface energy of the diffusion media has been changed in a negative way, operation of a fuel cell using the diffusion media may be unacceptable. For example, unstable operation of the fuel cell under wet conditions can occur due to flooding. Additionally, a decreased lifespan of the fuel cell stack can also be encountered when diffusion media having an unacceptable surface energy are used in a fuel cell.

Figure 4:
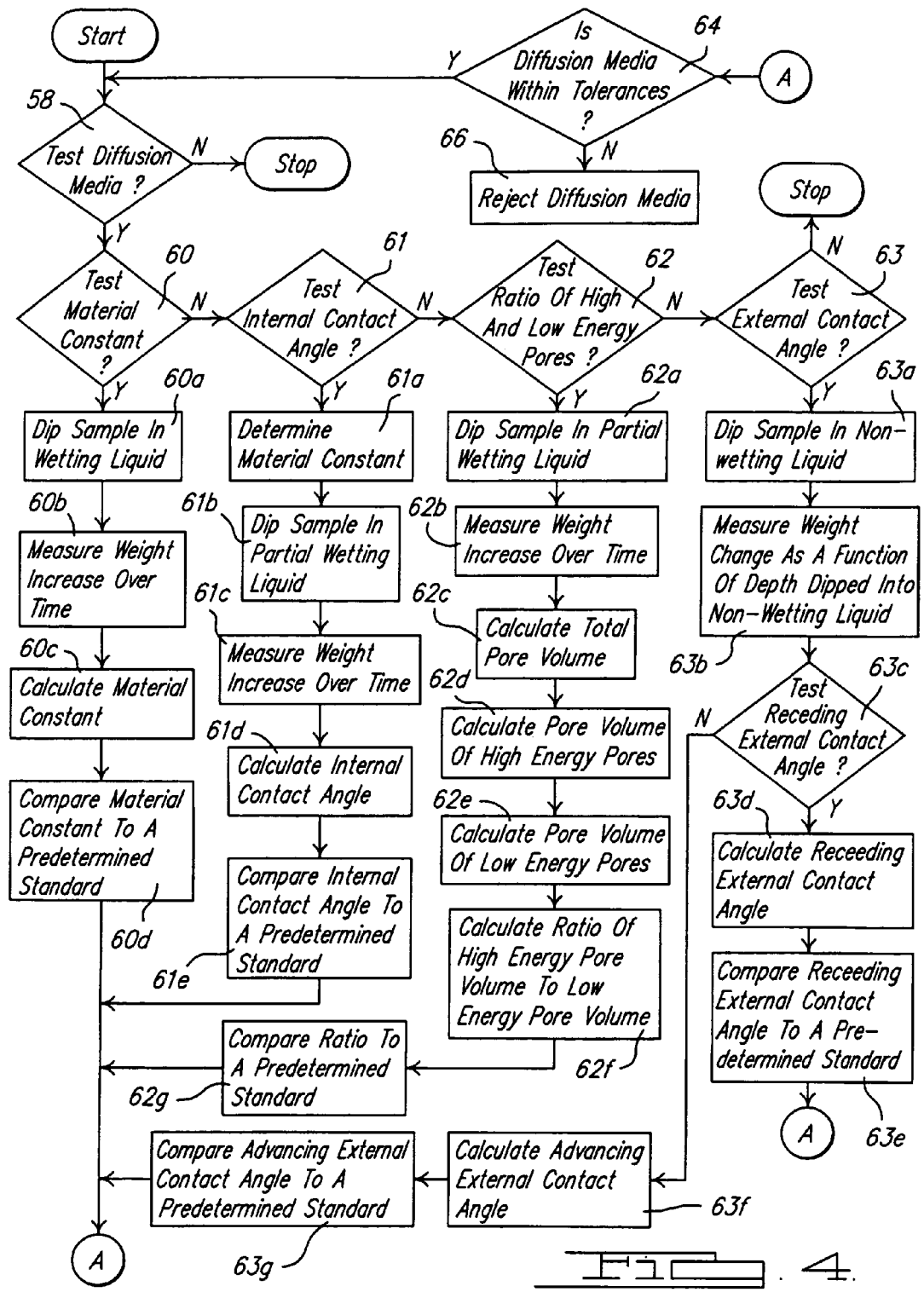
FIG. 4 is a flow chart showing the steps of the various methods that can be utilized to test and assess the quality of a diffusion media according to the principles of the present invention.

Referring to FIG. 4, the present invention provides various methods for quantitatively determining whether a diffusion media 30 and 32 is acceptable for use in fuel cell assembly 20. When it is desired to test a diffusion media, as indicated in step 58, four different tests, as indicated in steps 60, 61, 62 and 63, according to the principles of the present invention, are available to assess a quality and/or an acceptability of a diffusion media. These methods encompass various techniques, described below, that can be employed to quantitatively test the quality of the base material 46 and the various coatings and/or layers that are applied to the base material 46. Additionally, these techniques can be used to test the diffusion media 30 and 32 at various stages of manufacture to detect quality problems that may occur during the various stages. Additionally, these methods are directly related to the properties affecting the performance of diffusion media 30 and 32 in the fuel cell assembly 20. Thus, the methods provide for quality control by measuring liquid handling properties directly and quantitatively. The results are compared to predetermined standards to ascertain whether diffusion media 30 and 32 are within tolerances, as indicated in step 64, and suitable for use in fuel cell assembly 20, additional processing, and/or additional testing. If the diffusion media 30 and 32 are not within tolerances, the diffusion media is rejected, as indicated in step 66. The predetermined standards can be based on empirical data or theoretical considerations. The predetermined standards can be absolute values, ranges, minimums and maximums.

All of the tests 60, 61, 62 and 63 involve a sample 52 of diffusion media being placed in contact with a liquid 54. The liquid 54 used can be either a complete wetting liquid, a partial wetting liquid, or a non-wetting liquid depending upon the specific test and step being performed. A complete wetting liquid is a liquid that is adsorbed into and fills every pore in a solid and results in a contact angle θ for the solid of θ=0°, a partial wetting liquid is a liquid that is adsorbed into and fills only a portion of the pores in a solid and results in a contact angle θ for the solid of 0°<θ<90°, while a non-wetting liquid is a liquid that is not adsorbed into any pores in the solid and results in a contact angle θ for the solid of θ≧90°. Whether liquid 54 is a complete wetting liquid, a partial wetting liquid or a non-wetting liquid will depend on the nature of the liquid and the composition of the diffusion media. That is, for a given liquid, whether that liquid is a complete wetting liquid, a partial wetting liquid or a non-wetting liquid will depend upon the composition of the diffusion media. For example, methanol may be a complete wetting liquid for a diffusion media comprised of only base material 46 and a partial wetting liquid for a diffusion media comprised of base material 46 with a PTFE coating 48 while heptane may be a complete wetting liquid for a diffusion media comprised of either base material 46 only or base material 46 with a PTFE coating 48. Thus, the specific liquid chosen will vary. Preferably, a complete wetting liquid chosen has a surface tension of less than about 22 mN/m. Various liquids have these properties, such as n-hexane, n-heptane, and silicone oil, all of which can be used as a complete wetting liquid.

The methods of the present invention that are used to determine a quality of diffusion media 30 and 32 are based on the properties of diffusion media 30 and 32 that reflect upon its ability to transport fluids. The methods of the present invention utilize a number of different techniques to measure different properties of diffusion media 30 and 32 to determine whether diffusion media 30 and 32 are acceptable. One tool that is used in these methods is the Washburn adsorption technique which provides the basis for tests 60, 61 and 62. The Washburn adsorption technique is based on adsorption of a partially wetting liquid into the porous diffusion media 30 and 32. By measuring a weight increase over time an internal contact angle θ inside the porous diffusion media 30 and 32 can be calculated based on the Washburn theory. The Washburn theory states that when a liquid is brought in contact with a solid surface, the square of the mass of liquid which is adsorbed by capillary action is directly proportional to the adsorption time (length of time after the two are brought in contact). It is also dependent on physical properties of the liquid and solid and is expressed mathematically for a wetting liquid (either partial or complete) in Equation 1 as $$t = \frac{2\eta \cdot m^2}{C \cdot \delta^2 \cdot \pi^2 \cdot \sigma \cdot \cos\theta} \qquad \text{Equation 1}$$

where t is the time after the liquid is brought in contact with the solid, m is the mass (or weight) of liquid adsorbed, η is the liquid viscosity, C is the material constant of the solid, ρ is the liquid density, σ is the liquid surface tension, and θ is the internal contact angle of the solid surface for the wetting liquid. The material constant C is analogous to porosity, but is somewhat more specific because it is a function of mean pore radius (r) and number of pores in a given sample size (n). Its theoretical expression appears in Equation 2 as $$C = r_i^5 \cdot n_i^2 \qquad \text{Equation 2}$$

where $r_i$ is the mean pore radius and $n_i$ is the number of pores with mean pore radius $r_i$. Using Equations 1 and 2, it can quickly be determined that wetting time is inversely proportional to mean pore radius and number of pores. Furthermore, the wetting time is more sensitive to the radius of the pores than the actual number of pores present, indicated by the respective powers of these two parameters. Equation 1 also shows that wetting time increases with increasing internal contact angle θ, and that as θ approaches 90°, the theoretical time for adsorption approaches infinity (cos 90°=0). The internal contact angle θ and material constant C are determined experimentally by measuring a weight increase over time of a sample of diffusion media 30 and 32 dipped in a wetting liquid.

Figure 5:
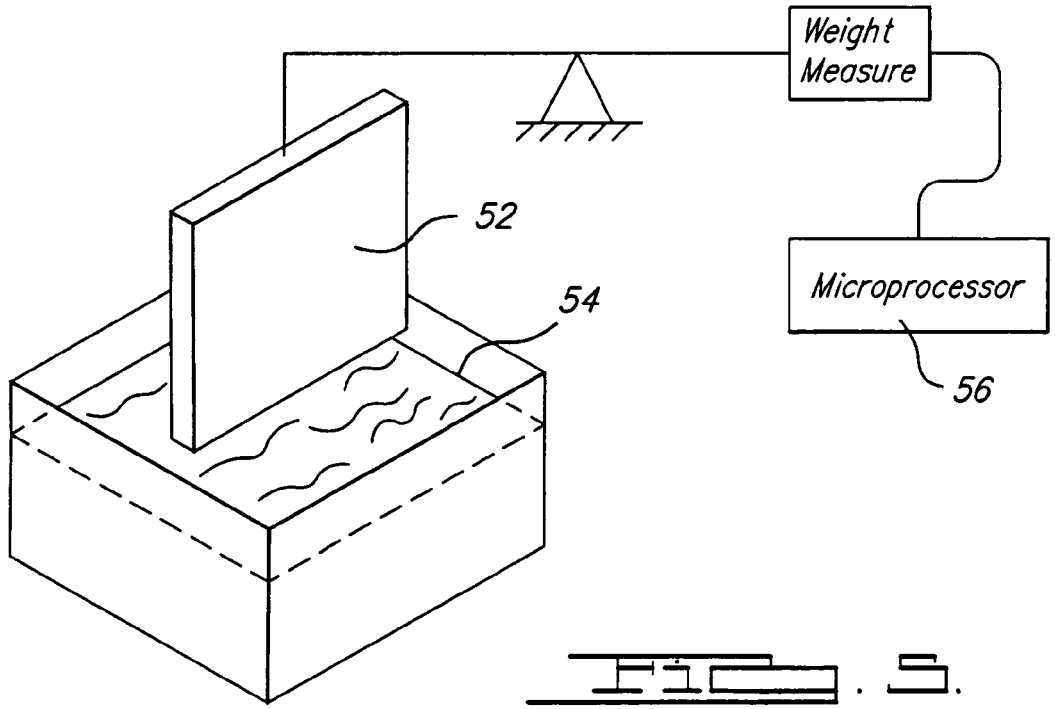
FIG. 5 is a simplified graphical representation of an arrangement that can be used to measure a weight increase over time or as a function of position of a diffusion media in contact with a liquid.

To measure the weight increase over time (when using the Washburn technique) a sample 52 of diffusion media is dipped into a liquid 54 so that an edge of sample 52 is in complete contact with liquid 54. FIG. 5 shows a graphical representation of an arrangement that can be used to measure the weight increase over time of sample 52. Sample 52 is attached to a mass detecting instrument, such as a tensiometer, by a wire and dipped into the liquid 54. The tensiometer measures the weight increase of the sample 52 and can be connected to a data collector, such as a microprocessor 56, which records the change in weight of sample 52 as a function of time.

As stated above, tests 60, 61 and 62 are all based on the Washburn adsorption technique. Test 60 comprises testing the material constant C of the diffusion media which is determined using steps 60a–60c, as described below. Test 61 comprises testing the internal contact angle θ of the diffusion media which requires that the material constant C be determined, as indicated in step 61a. Step 61a is accomplished by performing steps 60a–60c to determine the material constant C, as described below. Test 62 comprises testing a ratio of high and low energy pores in the diffusion media which does not require that the material constant C be determined. Thus, when it is desired to test a diffusion media using either tests 60 or 61, the first step is to determine the material constant C of the diffusion media, as indicated in steps 60a–60c of test 60 and step 61a of test 61.

The material constant C can be found by modifying Equation 1 to solve for C which results in Equation 3.

$$C = \frac{m^2}{t} \cdot \frac{2 \cdot \eta}{\delta^2 \cdot \pi^2 \cdot \sigma \cdot \cos\theta} \qquad \text{Equation 3}$$

Figure 6:
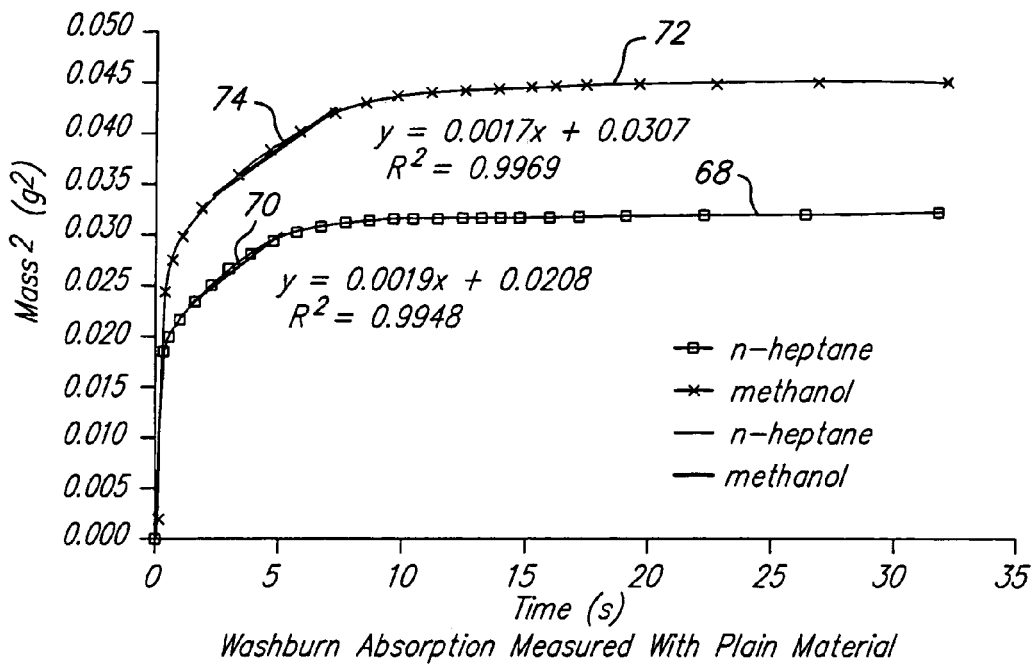
FIG. 6 is a graph of experimental data showing a mass increase squared over time for a diffusion media comprised of a base material only when dipped in n-heptane and methanol.

To solve for material constant C, sample 52 is dipped into a completely wetting liquid (internal contact angle θ=0°) which causes the term cos θ to drop out of Equation 3 (cos 0=1). The sample 52 is dipped in the complete wetting liquid so that at least an edge of sample 52 is in complete contact with the liquid and the weight increase over time is measured. Preferably, sample 52 is dipped in the complete wetting liquid in a way that an edge of sample 52 is strictly parallel with the liquid surface so that the edge is in complete contact with the liquid. A graph of the weight increase squared over time of the sample 52 in a complete wetting liquid, in this case n-heptane, is shown in FIG. 6 and indicated as curve 68. As can be seen, the weight increase in sample 52 approaches a maximum limit which represents a saturated condition wherein the complete wetting liquid has saturated the sample 52. As can be seen when looking at Equation 3, the term $$\frac{m^2}{t}$$

represents a slope of the curve 68. A portion 70, which is substantially linear, of curve 68 is used to calculate the slope $$\left(\frac{m^2}{t}\right)$$

which is then used to solve for material constant C. Portion 70 of curve 68 is chosen to reflect a substantially steady state adsorption of liquid 54 by sample 52. As can be seen, the portion 70 chosen begins at a time after the initial contact between the sample 52 and liquid 54 (to avoid meniscus effects and non-steady state adsorption) and ends prior to saturation (to avoid non-steady state adsorption) because all the other terms (properties) other than $$\frac{m^2}{t}$$

are known, with the calculation of the slope of portion 70, the material constant C for sample 52 when placed in a completely wetting liquid can be determined. The slope of portion 70 can be determined using a variety of statistical techniques. For example, a least squares fit technique can be performed to determine a slope for portion 70. If test 60 is being performed, the material constant C is compared to a predetermined standard, as indicated in step 60d, to ascertain if the diffusion media 30 and 32 is within tolerances, as indicated in step 64. If the material constant C is within tolerances, the diffusion media is acceptable and can be tested further, used in a fuel cell assembly 20, or further processed. If the material constant C is not within tolerances, the diffusion media is rejected, as indicated in step 66.

If test 61, testing internal contact angle θ, is being performed, the material constant C determined above is used (or determined using steps 60a–60c if test 60 was not performed). Once the material constant C has been obtained, an internal contact angle θ for sample 52 can be determined using Equation 1. Equation 1 can be rearranged to solve for the internal contact angle θ and expressed as shown in Equation 4.

$$\theta = \cos^{-1}\left[\frac{m^2}{t} \cdot \frac{2 \cdot \eta}{\delta^2 \cdot \pi^2 \cdot \sigma \cdot C}\right] \qquad \text{Equation 4}$$

To determine the internal contact angle θ, a sample 52 of diffusion media of substantially the same geometry and size as the sample used for the determination of the material constant, is dipped in a partial wetting liquid 54 so that at least an edge of sample 52 is in complete contact with the partial wetting liquid 54, as indicated in step 61b. The weight increase over time of sample 52 in the partial wetting liquid is measured and recorded, as indicated in step 61c. A graph of the weight increase squared versus time of sample 52, in this case a sample of diffusion media comprised solely of base material 46, in the partial wetting liquid, in this case methanol, is shown in FIG. 6 and indicated as curve 72. As can be seen, the weight increase in sample 52 approaches a maximum limit which represents a saturated condition, for this particular partial wetting liquid, wherein all pores that can be filled with the partial wetting liquid have been filled. The slope $$\left(\frac{m^2}{t}\right)$$

of curve 72 appears in Equation 4 along with material constant C and other known components/properties. Again, a portion 74, which is substantially linear, of curve 72 is used to calculate the slope $$\left(\frac{m^2}{t}\right)$$

which is then used to solve for the internal contact angle θ using Equation 4, as indicated in step 61*d*. Portion 74 is chosen based on the same criteria discussed above with reference to portion 70 of curve 68. Once internal contact angle θ has been obtained it is compared to a predetermined standard, as indicated in step 61*e*, to ascertain if the diffusion media from which sample 52 was taken is within tolerances, as indicated in step 64. If the internal contact angle θ is within tolerances, the diffusion media is acceptable and can be tested further, used in a fuel cell assembly 20, or further processed. If the internal contact angle θ is not within tolerances, the diffusion media is rejected, as indicated in step 66.

EXAMPLE 1

Testing of Base Material of Diffusion Media

A. Testing Material Constant C

A sample of base material 46 was tested to determine its material constant C and its internal contact angle θ. A sample of base material 46 was dipped in n-heptane (a complete wetting liquid) and the increase in weight squared as a function of time as a result of absorption of the complete wetting liquid is shown as curve 68 in FIG. 6. A portion 70 of curve 68 is used to determine the material constant C for the base material 46. Portion 70 comprises the data collected between approximately 1 to 5 seconds. An equation describing portion 70 was developed and is shown in FIG. 6. As can be seen based on the $R^2$ value, portion 70 is substantially linear. Using Equation 3, the data for n-heptane, and the slope of portion 70 of curve 68, all shown in Table 1, the material constant C for base material 46 is calculated as follows:

TABLE 1

| Property | | Property | |
|---|---|---|---|
| Viscosity [mPas] | 0.4105 | Surface tension [mN/m] | 20.4 |
| Density [Kg/m³] | 0.697 | Slope [g²/s] | 0.0019 |
| Contact angle | 0 (complete wetting liquid) | | |

$$C = \frac{m^2}{t} \cdot \frac{2 \cdot \eta}{\delta^2 \cdot \pi^2 \cdot \sigma \cdot \cos\theta}$$

$$= \frac{0.0019 \frac{g^2}{s}}{1000^2 \frac{g^2}{Kg^2}} \cdot \frac{2 \cdot 0.0004105 \frac{Ns}{m^2}}{0.697^2 \frac{kg^2}{m^6} \cdot \pi^2 \cdot 0.024 \frac{N}{m} \cdot \cos(0)}$$

$$= 1.59 \times 10^{-11} \text{ m}^5$$

The material constant C can then be compared to a predetermined standard to ascertain the quality of base material 46.

B. Testing Internal Contact Angle θ

A sample 52 of the same base material 46 was dipped in methanol, a partial wetting liquid, and a resulting plot of the increase in weight squared as a function of time is shown as curve 72 in FIG. 6. A portion 74 (between approximately 3 and 8 seconds) of curve 72 is used to test the internal contact angle θ. A curve fit for portion 74 was developed and is shown in FIG. 6. The slope of portion 74 is shown in Table 2 along with the properties of methanol and the material constant C of the diffusion media as calculated above. Using the data in Table 2 and Equation 4, the internal contact angle θ of base material 46 when dipped in methanol is calculated as shown below.

TABLE 2

| Property | | Property | |
|---|---|---|---|
| Viscosity [mPas] | 0.591 | Surface tension [mN/m] | 22.4 |
| Density [Kg/m³] | 0.7914 | Slope [g²/s] | 0.0017 |
| Material Constant [m⁵] | 1.59 × 10⁻¹¹ | | |

$$\Theta = \cos^{-1}\left[\frac{0.0017 \frac{g^2}{s}}{1000^2 \frac{g^2}{Kg^2}} \cdot \frac{2 \cdot 0.000591 \frac{Ns}{m^2}}{0.7914^2 \frac{Kg^2}{m^6} \cdot \pi^2 \cdot 0.024 \frac{N}{m} \cdot 1.59 \times 10^{-11} m^5}\right] =$$

$$\cos^{-1}[0.912] \Rightarrow \Theta = 24.2°$$

The internal contact angle θ can then be compared to a predetermined standard to ascertain the quality of base material 46.

Some types of diffusion media may have properties and/or characteristics, such as high energy pores and low energy pores, which adsorb a partial wetting liquid at different rates. The different rates of adsorption by the high and low energy pores can be seen in a curve of the weight increase squared versus time which produces two distinct substantially linear portions along the curve instead of a single substantially linear portion as described above. For example, when diffusion media 30 and 32 comprises base material 46 having a PTFE coating 48 and a microporous layer 50, diffusion media 30 and 32 will have both high energy pores and low energy pores. The terms high energy pores and low energy pores are relative terms wherein high energy pores refer to pores that adsorb a specific liquid more quickly than low energy pores. Diffusion media exhibiting this behavior can also be quantitatively tested using the methods of the present invention. Specifically, material constant test 60, internal contact angle test 61 and a ratio of high and low energy pores test 62, described below, can be used to quantitatively test the diffusion media. Material constant C is determined using steps 60*a*–60*c* described above and does not change due to this different behavior of the diffusion media. Thus, test 60 is performed in the same manner discussed above and is not discussed further.

Figure 7:
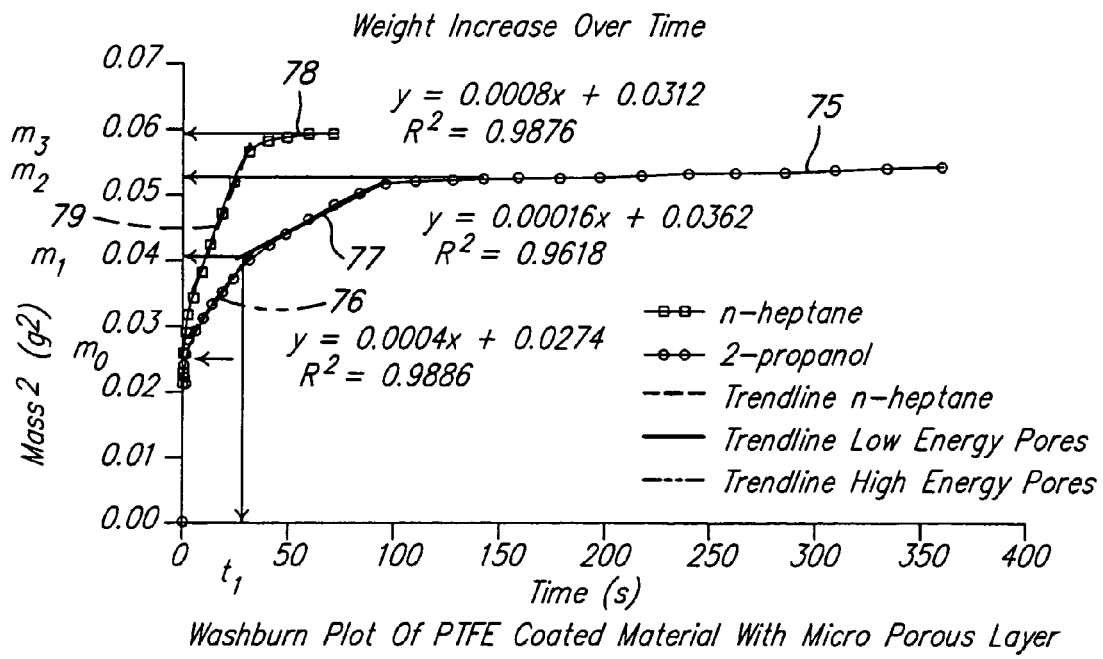
FIG. 7 is a graph of experimental data of a mass increase squared over time of a PTFE coated diffusion media with a microporous layer when dipped in n-heptane and 2-propanol.

The phenomenon of high and low energy pores is shown in FIG. 7, which is a plot of weight increase squared versus time of a sample 52 of a diffusion media, having a PTFE coating 48 and a microporous layer 50 which was dipped in a partial wetting liquid, in this case 2-propanol, and indicated as curve 75. As can be seen, curve 75 comprises two distinct substantially linear portions identified as a first portion 76 and a second portion 77. As can be seen, the slope of first portion 76 is steeper than the slope of second portion 77. This is due to the fact that first portion 76 represents adsorption of the 2-propanol by both the high energy and low energy pores while second portion 77 represents further adsorption primarily caused by the low energy pores only as the high energy pores have substantially reached a saturation point. That is, because the high energy pores adsorb the 2-propanol quicker than the low energy pores, the high energy pores will reach a saturation condition before the low energy pores reach saturation. As a result, the second portion 77 of curve 75 has a smaller slope reflective of adsorption by the low energy pores and not the high energy pores. The first and second portions 76 and 77 of curve 75 are chosen using similar criteria discussed above in reference to portion 70 of curve 68. Additionally, first and second portions 76 and 77 can also be chosen so as to have respective ending and starting points that avoid the transition period where the primary adsorption mode changes from adsorption by both high and low energy pores to adsorption by low energy pores.

When it is desired to test the internal contact angle θ of a diffusion media having high and low energy pores, test 61 can be performed by testing the internal contact angle θ of the low energy pores and/or the internal contact angle θ of the high energy pores. That is, first and second portions 76 and 77 can be used to determine the internal contact angle θ for the low energy pores and the high energy pores. Specifically, the slope of the second portion 77 can be used in conjunction with Equation 4 and the material constant C, determined in step 61a, to calculate an internal contact angle θ for the low energy pores as indicated in step 61d and described above. The slope of the first portion 76 requires further data manipulation before an internal contact angle θ for the high energy pores can be calculated due to the fact that the first portion 76 is comprised of adsorption of the partial wetting liquid by both high and low energy pores. The portion of the slope of the first portion 76 attributable to adsorption only by the high energy pores can be determined by subtracting the slope of second portion 77 from the slope of first portion 76. The slope of the high energy pores can then be used in conjunction with Equation 4 and material constant C, determined in step 61a, to calculate the internal contact angle θ for the high energy pores, as indicated in step 61d and described above.

EXAMPLE 2

Testing a PTFE Coated Diffusion Media with a Microporous Layer

A. Testing Material Constant

A sample 52 of a PTFE coated diffusion media with a microporous layer was dipped in n-heptane, a complete wetting liquid, and an increase in weight over time was measured. The results were plotted in FIG. 7 as a weight increase squared over time and indicated as curve 78. Curve 78 has a portion 79, which is substantially linear, that is used to determine material constant C. As was discussed above, an equation describing portion 79 of curve 78 is developed and is shown in FIG. 7. The slope of portion 79 of curve 78 and the properties of n-heptane are shown below in Table 2. Using the data in Table 2 and Equation 3, material constant C for the PTFE coated diffusion media with a microporous layer is calculated as follows.

TABLE 2

| Property | | Property | |
|---|---|---|---|
| Viscosity [mPas] | 0.4105 | Surface tension [mN/m] | 20.4 |
| Density [Kg/m³] | 0.697 | Slope [g²/s] | 0.0008 |
| Contact angle | 0 | | |
| | (complete wetting liquid) | | |

Applied to equation 3:

$$C = \frac{m^2}{t} \cdot \frac{2\eta \cdot}{\delta^2 \cdot \pi^2 \cdot \sigma \cdot \cos\Theta} =$$

$$\frac{0.0008 \frac{g^2}{s}}{1000^2 \frac{g^2}{Kg^2}} \cdot \frac{2 \cdot 0.0004105 \frac{N}{m^2} s}{0.697^2 \frac{kg^2}{m^6} \cdot \pi^2 \cdot 0.0204 \frac{N}{m} \cdot \cos(0)} = 0.67 \times 10^{-11} \, m^5$$

Material constant C can then be compared to a predetermined standard to ascertain if the PTFE coated diffusion media with a microporous layer is within tolerances and suitable for further processing, testing and/or use in a fuel cell assembly 20.

B. Testing Internal Contact Angle

Once material constant C has been determined, an internal contact angle θ for the PTFE coated diffusion media with a microporous layer can be determined by conducting test 61. A different sample 52 of the same PTFE coated diffusion media with a microporous layer was dipped in 2-propanol, a partial wetting liquid, and an increase in weight over time was measured. The results are plotted in FIG. 7 as curve 75, which is a plot of the increase in weight squared over time. As was mentioned above, curve 75 has a first and second portion 76 and 77 that have distinct and different slopes. Equations describing first and second portions 76 and 77 were developed and are shown in FIG. 7. The difference between the slopes of portions 76 and 77, as was described above, is due to the fact that first portion 76 represents the 2-propanol being adsorbed by both the high and low energy pores while second portion 77 is reflective of the 2-propanol being adsorbed primarily by the low energy pores due to the high energy pores having substantially obtained a saturated condition. The slope of second portion 77 of curve 75 can be used to determine the internal contact angle θ for the low energy pores using the data in Table 3 and Equation 4 and is calculated below. To determine an internal contact angle θ for the high volume pores, the contribution to the slope of first portion 76 of curve 75 due to the high energy pores adsorbing the 2-propanol needs to be determined. The slope of second portion 77 of curve 75 is subtracted from the slope of first portion 76 of curve 75 to calculate the slope of first portion 76 attributable to adsorption by the high energy pores and is shown in Table 3 below. The properties of 2-propanol and the slopes for the high and low energy pores are shown in Table 3. Using the data in Table 3 and Equation 4, the internal contact angle θ for both the low and high energy pores is calculated as follows:

TABLE 3

| Property | | Property | |
|---|---|---|---|
| Viscosity [mPas] | 2.39 | Surface tension [mN/m] | 20.93 |
| Material Constant [m$^5$] | 0.67 × 10$^{-11}$ | Slope Low Energy Pores [g$^2$/s] | 0.00016 |
| Density [Kg/m$^3$] | 0.7809 | Slope High Energy Pores [g$^2$/s] | 0.00024 |

$$\Theta_{Low\ Energy} =$$

$$\cos^{-1}\left[\frac{0.00016\ \frac{g^2}{s}}{1000^2\ \frac{g^2}{Kg^2}} \cdot \frac{2 \cdot 0.00239\ \frac{Ns}{m^2}}{0.7809^2\ \frac{Kg^2}{m^6} \cdot \pi^2 \cdot 0.02039\ \frac{N}{m} \cdot 0.67 \times 10^{-11}\ m^5}\right] =$$

$$\cos^{-1}[0.92] = \ > \Theta_{low\ energy} = 23.1°$$

$$\Theta_{High\ Energy} =$$

$$\cos^{-1}\left[\frac{0.00024\ \frac{g^2}{s}}{1000^2\ \frac{g^2}{Kg^2}} \cdot \frac{2 \cdot 0.00239\ \frac{Ns}{m^2}}{0.7809^2\ \frac{Kg^2}{m^6} \cdot \pi^2 \cdot 0.02039\ \frac{N}{m} \cdot 0.67 \times 10^{-11}\ m^5}\right] =$$

$$\cos^{-1}[1.09] = \ > \Theta_{high\ energy} = \text{undefined}$$

The internal contact angle θ for the low energy pores can be compared to a predetermined standard to ascertain if the PTFE coated diffusion media with a microporous layer is within tolerances and suitable for use in a fuel cell assembly 20, for additional processing, and/or additional testing. The internal contact angle θ for the high energy pores, however, is undefined. This indicates that the internal contact angle θ of the high energy pores cannot be measured with 2-propanol as the partial wetting liquid. That is, 2-propanol is a complete wetting liquid with respect to the high energy pores in this particular PTFE coated diffusion media with a microporous layer. Thus, if it is desired to determine an internal contact angle θ for the high energy pores, a partial wetting liquid other than 2-propanol will need to be used.

When the diffusion media contains both high and low energy pores, another test according to the principles of the present invention is available to quantitatively ascertain a property of the diffusion media, as indicated in step 62. In the test of step 62, a ratio of high and low energy pore volumes is determined and used to quantitatively ascertain the quality of the diffusion media. Specifically, the total pore volume of high energy pores and the total pore volume of low energy pores within a diffusion media are determined, as indicated in steps 62d and 62e, and a ratio of the two pore volumes is calculated, as indicated in step 62f, and compared to a predetermined standard, as indicated in step 62g, to ascertain whether the diffusion media has acceptable properties, as indicated in step 64. To determine the pore volume of high energy pores and low energy pores a sample 52 of the diffusion media is first dipped in a partial wetting liquid, as indicated in step 62a and described above with reference to step 61b, and a weight increase over time of sample 52 is measured, as indicated in step 62b and described above with reference to step 61c, and a total pore volume of diffusion media 30 and 32 is calculated, as indicated in step 62c. The total pore volume is determined by measuring the total weight increase when sample 52 is saturated by the partial wetting liquid, subtracting the weight increase caused by initial effects between sample 52 and the liquid and then dividing by the density of the partial wetting liquid, as shown in Equation 5

$$V_{total(L)} = \frac{m_{SL} - m_{IL}}{\delta_L} \quad \text{Equation 5}$$

where $V_{total(L)}$ is the total pore volume of sample 52 when dipped in liquid L, $m_{SL}$ is the weight increase of sample 52 due to saturation of sample 52 with liquid L, $m_{IL}$ is the weight increase of sample 52 due to initial effects between sample 52 and the liquid L and not due to adsorption, and $\delta_L$ is the density of liquid L.

After determining the total pore volume of sample 52 for the liquid 54, the volume of high energy pores is calculated, as indicated in step 62d. The volume of high energy pores is calculated by determining the weight increase in sample 52 due to adsorption of liquid 54 by the high energy pores and dividing by the density of liquid 54. To determine the weight increase in sample 52 caused by adsorption of liquid 54 by the high energy pores, first portion 76 of curve 75 is used. First portion 76 represents a weight increase squared in sample 52 due to adsorption of liquid 54 by both the high and low energy pores and due to initial effects between sample 52 and liquid 54. Therefore, the contribution attributable to the low energy pores and attributable to the initial effects needs to be subtracted to ascertain the weight increase due to adsorption only by the high energy pores. To accomplish this, the weight increase, $m_{IL}$, due to initial effects between sample 52 and liquid 54 and the weight increase due to adsorption by low energy pores is subtracted from the weight increase due to adsorption by both the high and low energy pores. The weight increase due to initial effects between sample 52 and liquid 54 is the square root of $m_0$ in FIG. 7. $M_0$ is the initial weight increase squared of sample 52 when initially put in contact with liquid 54. The weight increase due to adsorption by both the high and low energy pores is the square root of $m_1$ in FIG. 7. $M_1$ is the weight increase squared of sample 52 substantially at the transition from adsorption by both the high and low energy pores to adsorption primarily by the low energy pores. The weight increase caused by adsorption by low energy pores is ascertained from the slope of second portion 77 of curve 75 and multiplying it by $t_1$, the time to reach $m_1$. The resulting mass increase due to adsorption by the high energy pores is then divided by the density of the liquid to determine the volume of high energy pores and is represented by Equation 6

$$V_{highenergy(L)} = \frac{\sqrt{m_1 - m_0 - (a_{low} \cdot t_1)}}{\delta_L} \quad \text{Equation 6}$$

where $V_{highenergy\ (L)}$ is the pore volume of high energy pores, $m_1$ is the squared weight increase due to both high and low energy pores adsorbing liquid L, $m_0$ is the squared weight increase due to initial effects between sample 52 and liquid L, $a_{low}$ is the slope of the squared weight increase over time due to adsorption by low energy pores (slope of second portion 77 of curve 75), $t_1$ is the time to reach $m_1$, and $\delta_L$ is the density of liquid L.

Once the pore volume of the high energy pores has been calculated, the volume of low energy pores is calculated, as indicated in step 62e, by subtracting the volume of high energy pores from the total pore volume as shown in Equation 7

$$V_{lowenergy(L)} = V_{total(L)} - V_{highenergy(L)} \quad \text{Equation 7}$$

where $V_{lowenergy(L)}$ is the volume of low energy pores for liquid L, $V_{total\,(L)}$ is the total pore volume for liquid L, and $V_{highenergy(L)}$ is the volume of high energy pores for liquid L. The ratio of the volume of high energy pores to the volume of low energy pores is then calculated, as indicated in step 62f, using Equation 8

$$\eta_{(L)} = \frac{V_{high\ energy(L)}}{V_{low\ energy(L)}} \quad \text{Equation 8}$$

where $\rho_{(L)}$ is the ratio of the volume of high energy pores to the volume of low energy pores. This ratio can then be compared to a predetermined standard, as indicated in step 62g, and whether the diffusion media is within tolerances is ascertained, as indicated in step 64. If the ratio is within tolerances, the diffusion media is acceptable and can be tested further, used in a fuel cell assembly 20, or further processed. If the ratio is not within tolerances, the diffusion media is rejected, as indicated in step 66. While the ratio $\rho_{(L)}$ described above is a ratio of the pore volumes of high energy pores to low energy pores, it should be understood that a ratio of the pore volumes of low energy pores to high energy pores can also be used and compared to an appropriate predetermined standard to ascertain a quality of the diffusion media.

EXAMPLE 3

Testing a PTFE Coated Diffusion Media with a Microporous Layer

Testing Ratio of High and Low Energy Pores

The same PTFE coated diffusion media with a microporous layer that was tested in Example 2, can also be quantitatively evaluated by testing a ratio of high and low energy pores. To test the ratio of high and low energy pores, a sample 52 of the PTFE coated diffusion media with microporous layer is dipped in a partial-wetting liquid while an increase in weight over time is measured. These steps were done in Example 2 and resulted in curve 75 shown in FIG. 7. The next step is to determine the total pore volume. The increase in weight squared when both the high and low energy pores are saturated is reflected as $m_2$ in FIG. 7 while the increase in weight squared at a time when the high energy pores have just reached a saturated condition is represented as $m_1$. The increase in weight squared caused by initial effects between sample 52 and the partial-wetting liquid is represented as $m_0$ in FIG. 7. The numerical values of $m_1$, $m_2$ and $m_0$ are shown in Table 4 below along with the properties for 2-propanol. Using Equation 5 in conjunction with the data in Table 4, the total pore volume for the PTFE coated diffusion media with a microporous layer is calculated as follows:

TABLE 4

| Property | | Property | |
|---|---|---|---|
| Density [g/cm³] | 0.781 | $t_1$[s] | 31 |
| $m_1$[g²] | 0.040804 | $a_{low}\left[\dfrac{g^2}{s}\right]$ | 0.00016 |
| $m_2 = m_{SL}{}^2$ [g²] | 0.051984 | $m_0 = m_{IL}{}^2$ [g²] | 0.025 |

$$V_{total} = \frac{m_{SL} - m_{IL}}{\delta} = \frac{\sqrt{m_2 - m_0}}{\delta} = \frac{\sqrt{0.051984\ g^2 - 0.025\ g^2}}{0.781\ \frac{g}{cm^3}} = 0.210\ cm^3$$

Now that the total pore volume has been determined, the volume of high energy pores can be determined. Using Equation 6 and the data in Table 4, the volume of high energy pores is calculated as follows:

$$V_{high\ energy} = \frac{\sqrt{m_1 - m_0 - (a_{low} \cdot t_1)}}{\delta} = \frac{\sqrt{0.040804\ g^2 - 0.025\ g^2 - 0.00016\ \frac{g^2}{s} \cdot 31_s}}{0.781\ \frac{g}{cm^3}} = 0.133\ cm^3$$

The volume of the low energy pores is now calculated using Equation 7 as follows:

$$V_{low\ energy} = V_{total} - V_{high\ energy} = 0.210\ cm^3 - 0.133\ cm^3 = 0.077\ cm^3$$

Finally, the ratio of the volume of high energy pores to the volume of low energy pores is calculated using Equation 8 as follows:

$$\eta = \frac{V_{high\ enery}}{V_{low\ energy}} = \frac{0.133\ cm^3}{0.077\ cm^3} = 1.73$$

The ratio $\rho$ can then be compared to a predetermined standard to ascertain if the PTFE coated diffusion media with a microporous layer is within tolerances and suitable for use in a fuel cell assembly 20, for further processing, or for further testing.

In another aspect of the present invention, a different method of quantitatively determining a quality of diffusion media 30 and 32 is used. This method tests an external contact angle θ of the diffusion media, as indicated in step 63. The external contact angle θ is calculated, as indicated in steps 63d and 63f, and compared to an appropriate predetermined standard, as indicated in steps 63e and 63g, and whether the diffusion media is within tolerances is ascertained, as indicated in step 64. The method of testing the external contact angle θ is based on the Wilhelmy adsorption technique which determines an external contact angle θ between a non-wetting liquid and a solid by measuring a weight change caused by dipping sample 52 in a non-wetting liquid. This technique is fast and inexpensive to run and measures liquid interaction at the surface of the diffusion media, which is the primary mechanism for flooding of a catalyst layer.

If it is desired to test the external contact angle θ, as indicated in step 63, a portion of a sample 52 of diffusion media is dipped in a non-wetting liquid 54, as indicated in step 63a. While sample 52 is being placed in and removed from the non-wetting liquid, a weight change in sample 52 is measured and recorded as a function of the depth or position of sample 52 in the non-wetting liquid, as indicated in step 63b. The arrangement shown graphically in FIG. 5, adapted to measure a weight change as a function of position, can be used to dip sample 52 into and out of the non-wetting liquid 54 while recording the change in weight of sample 52.

A graph of a weight change as a function of position of sample 52 of diffusion media, in this case a diffusion media comprised of base material 46 having a PTFE coating 48 and a microporous layer 50, dipped in a non-wetting liquid, in this case water, is shown in FIG. 8. As can be seen, the graph has two distinct curves that correspond, respectively, to advancing sample 52 into the non-wetting liquid, indicated as advancing curve 80, and removing or receding sample 52 from the non-wetting liquid, indicated as receding curve 82. Advancing curve 80 has an advancing non-linear first portion 84 and an advancing substantially linear second portion 86. Advancing first portion 84 corresponds to a meniscus forming between sample 52 and the non-wetting liquid as sample 52 is advanced or immersed into the non-wetting liquid. Similarly, receding curve 82 has a receding non-linear first portion 88 and a receding substantially linear second portion 90. Receding first portion 88 corresponds to a meniscus forming between sample 52 and the non-wetting liquid when sample 52 is receding or removed from the non-wetting liquid. Equations describing the second portions 86 and 90 are determined using statistical techniques, such as those discussed above in reference to portion 70 of curve 68. The first portions 84 and 88 that correspond to meniscus formation are not used in determining an external contact angle θ for sample 52. Rather, second portions 86 and 90 can be used to determine, respectively, an advancing external contact angle $\theta_a$ and a receding external contact angle $\theta_r$ for sample 52 based on the Wilhelmy technique and the equations describing the characteristics of the second portions 86 and 90, as indicated in step 63c.

Specifically, the external contact angle θ of sample 52 when dipped in a non-wetting liquid is determined using the Wilhelmy equation which is shown in Equation 9

$$\theta = \cos^{-1}\left[\frac{m_\sigma \cdot g}{L_{WL} \cdot \sigma}\right]$$ Equation 9 where θ is the external contact angle, $m_\sigma$ is the weight change caused by the solid/liquid interaction between sample 52 and the non-wetting liquid, $L_{WL}$ is the wetted length (2·(d+w)) where d is the thickness of sample 52 and w is the width of sample 52, σ is the surface tension of the non-wetting liquid, and g is the gravity constant. The advancing and receding weight changes ($m_\sigma$) caused by the interaction between sample 52 and the non-wetting liquid are determined by setting the position to zero (x=0) and solving the equations that describe the second portions of the respective advancing and receding curves 80 and 82. In other words, the non-varying portion of the equations that describe second portions 86 and 90 are used as the respective weight change ($m_\sigma$) in calculating the advancing and receding external contact angles θ. Thus, an advancing external contact angle $\theta_{adv}$ and/or a receding external contact angle $\theta_{rec}$, as indicated in steps 63d and 63f, can be calculated for diffusion media 30 and 32 based on testing sample 52 in a non-wetting liquid. The resulting external contact angles θ are then compared to respective predetermined standards, as indicated in steps 63e and 63g. Based on the comparisons to the appropriate predetermined standards, whether the diffusion media is within tolerances is then determined, as indicated in step 64. If the external contact angle θ is within tolerances, the diffusion media is acceptable and can be tested further, used in a fuel cell assembly 20, or further processed. If the external contact angle θ is not within tolerances, the diffusion media is rejected, as indicated in step 66.

EXAMPLE 4

Testing a PTFE Coated Diffusion Media with a Microporous Layer

Testing External Contact Angle

A sample 52 of a PTFE coated diffusion media with a microporous layer was dipped in water, a non-wetting liquid, while the change in weight as a function of position of the sample was measured. The result of measuring the change in weight as a function of position is shown in FIG. 8 and is represented by advancing curve 80 and receding curve 82. As was discussed above, the second portions 86 and 90 of the respective advancing and receding curves 80 and 82 are used to determine the external contact angle θ. An equation describing the advancing second portion 86 of advancing curve 80 was developed and is shown in FIG. 8. An equation describing the receding second portion 90 of receding curve 82 was also developed and is shown in FIG. 8. The known properties of the sample (i.e., wetted length, thickness, and width) along with the surface tension of the water and the gravity constant are known and shown in Table 5 along with the weight change $m_\sigma$ caused by the interaction between the water and the sample. Using the data in Table 5 in conjunction with Equation 9, the advancing internal contact angle $\theta_{adv}$ and receding internal contact angle $\theta_{rec}$ are calculated as follows:

TABLE 5

| Property | Advancing | Receding |
|---|---|---|
| $m_\sigma$ | −0.5846 | −0.084 g |
| Wetting Length | 82.66 mm | |
| Surface Tension | 72.8 mN/m | |
| Gravity constant | 9.81 m/s² | |

Advancing $\Theta_{adv} = \cos^{-1}\left[\frac{m_\sigma \cdot g}{L \cdot \sigma}\right] =$ $\cos^{-1}\left[\frac{-0.5846 \text{ g} \cdot 9.81 \frac{m}{s^2}}{82.66 \times 10^{-3} \text{ m} \cdot 72.8 \frac{gm}{s^2 m}}\right] = \cos^{-1}[-0.956] = > \Theta_{adv} = 162°$ Receding $\Theta_{rec} = \cos^{-1}\left[\frac{m_\sigma \cdot g}{L \cdot \sigma}\right] =$ -continued $$\cos^{-1}\left[\frac{-0.084 \text{ g} \cdot 9.81 \frac{m}{s^2}}{82.66 \times 10^{-3} \text{ m} \cdot 72.8 \frac{gm}{s^2 m}}\right] = \cos^{-1}[-0.137] => \Theta_{adv} = 97.8°$$

The advancing external contact angle $\theta_{adv}$ and/or the receding external contact angle $\theta_{rec}$ can then be compared to an appropriate predetermined standard to ascertain if the PTFE coated diffusion media with microporous layer is within tolerances and suitable for use in a fuel cell assembly 20, further processing, and/or further testing.

In addition to providing a quantitative evaluation of the quality of a diffusion media, the testing methods of the present invention facilitate the manufacture of a diffusion media having various coatings and/or layers. That is, the quantitative measure of the properties of the diffusion media can be used to refine further processing steps. For example, the material constant and/or the contact angle can be used to provide a required length of time for base material 46 to be in a dispersion containing PTFE particles to apply a PTFE coating of a specified concentration on base material 46. Additionally, the material constant and/or contact angles can be used to aid in the application of a microporous coating. For example, the material constant and/or contact angles can be used to determine a required composition of a solvent used to apply the microporous layer 50. Thus, the methods of the present invention can be used to aid in the processing and manufacture of a diffusion media.

The above described various methods of the present invention enable different properties of the diffusion media to be quantitatively evaluated along with allowing diffusion media of various compositions to be quantitatively evaluated. The various testing method according to the present invention include: (1) testing the material constant; (2) testing an internal contact angle; (3) testing a ratio of high and low energy pores; and (4) testing an external contact angle (receding and/or advancing). Additionally, various examples have been provided to further explain and clarify the different testing methods of the present invention and the applicability of these methods to diffusion media having various coatings and/or layers. It should be understood that the examples shown are for purposes of illustration only and should not be construed to limit the scope or applicability of the methods of the present invention to diffusion media having coatings and/or layers different from those in the examples.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of determining a quality of a diffusion media for use in a fuel cell, the method comprising the steps of:
   (a) determining an internal contact angle of a diffusion media based on imbibing of a partial wetting liquid by said diffusion media;
   (b) comparing said internal contact angle with a predetermined standard; and
   (c) ascertaining a quality of said diffusion media based on said comparison,
   wherein step (a) further comprises determining a relationship between mass increase and time duration of imbibing.

2. The method of claim 1, wherein step (a) further comprises deriving said internal contact angle based on said relationship.

3. The method of claim 1, wherein said time duration is a time period prior to saturation of said diffusion media by said liquid.

4. The method of claim 1, wherein said relationship exhibits a distinct change in slope between a first portion of said relationship characteristic of high and low energy pores imbibing said fluid and a second portion of said relationship characteristic of low energy pores imbibing said fluid and step (a) further comprises determining an internal contact angle for high energy pores based on said first portion.

5. The method of claim 1, wherein said relationship exhibits a distinct change in slope between a first portion of said relationship characteristic of high and low energy pores imbibing said fluid and a second portion of said relationship characteristic of low energy pores imbibing said fluid and step (a) further comprises determining an internal contact angle for low energy pores based on said second portion.

6. The method of claim 1, wherein said partial wetting liquid is isopropanol.

7. The method of claim 1, wherein said predetermined standard is a range of acceptable internal contact angles.

8. The method of claim 1, wherein said predetermined standard is based upon empirical data.

9. The method of claim 1, wherein said partial wetting liquid is methanol.

10. The method of claim 1, further comprising accepting said diffusion media based upon said comparison.

11. The method of claim 1, wherein (a) includes determining a material constant for said diffusion media based upon imbibing of a wetting liquid by said diffusion media.

12. A method of testing a diffusion media for use in a fuel cell, the method comprising the steps of:
    (a) determining a relationship between a mass increase and time duration of imbibing of a liquid by a diffusion media;
    (b) determining an internal contact angle of said diffusion media based on said relationship;
    (c) comparing said internal contact angle with an empirically based predetermined standard; and
    (d) ascertaining an acceptability of said diffusion media based upon said comparison.

13. The method of claim 12, wherein said liquid is a partial wetting liquid for said diffusion media.

14. The method of claim 12, wherein (b) includes using a substantially linear portion of said relationship to determine said internal contact angle.

15. The method of claim 12, wherein prior to saturation said relationship exhibits a distinct change in slope between a first portion of said relationship characteristic of a faster rate of imbibing said liquid and a second portion of said relationship characteristic of a slower rate of imbibing said liquid and (b) further comprises determining an internal contact angle based on said first portion.

16. The method of claim 15, wherein (b) comprises determining an internal contact angle for high energy pores based on said first portion.

17. The method of claim 12, wherein prior to saturation said relationship exhibits a distinct change in slope between a first portion of said relationship characteristic of a faster rate of imbibing said liquid and a second portion of said relationship characteristic of a slower rate of imbibing said liquid and (b) further comprises determining an internal contact angle based on said second portion.

18. The method of claim 17, wherein (b) comprises determining an internal contact angle for low energy pores based on said second portion.

19. A method of testing a diffusion media for use in a fuel cell, the method comprising the steps of:
 (a) ascertaining a quality of a diffusion media based upon a comparison of an internal contact angle of said diffusion media to a predetermined standard;
 (b) accepting said diffusion media for at least one of use in a fuel cell and application of a coating to said diffusion media based upon said ascertained quality; and
 (c) rejecting said diffusion media based upon said ascertained quality if said diffusion media quality is unacceptable.

* * * * *